(12) United States Patent
Goel

(10) Patent No.: US 8,507,233 B1
(45) Date of Patent: Aug. 13, 2013

(54) NANOBIOFUEL PRODUCTION USING NANOSCALE CONTROL METHODS AND MATERIALS

(75) Inventor: Anita Goel, Cambridge, MA (US)

(73) Assignee: Nanobiosym, Inc., Cambridge, MA (US)

( * ) Notice: Subject to any disclaimer, the term of this patent is extended or adjusted under 35 U.S.C. 154(b) by 0 days.

(21) Appl. No.: 12/828,219

(22) Filed: Jun. 30, 2010

Related U.S. Application Data

(60) Provisional application No. 61/222,100, filed on Jun. 30, 2009.

(51) Int. Cl.
*C12P 7/06* (2006.01)
*C12P 7/00* (2006.01)

(52) U.S. Cl.
USPC .......................................... 435/161; 435/132

(58) Field of Classification Search
USPC ................................................ 435/132, 161
See application file for complete search history.

(56) References Cited

U.S. PATENT DOCUMENTS

| | | | |
|---|---|---|---|
| 6,346,252 B1 * | 2/2002 | Moigne | 424/195.17 |
| 7,905,049 B2 * | 3/2011 | Erd | 47/1.4 |
| 2008/0155888 A1 * | 7/2008 | Vick et al. | 44/308 |
| 2010/0196971 A1 * | 8/2010 | Lin et al. | 435/134 |
| 2010/0279354 A1 * | 11/2010 | de Crecy | 435/71.1 |

OTHER PUBLICATIONS

Olle et al. (Enhancement of Oxygen Transfer in Fermentation by Use of Functionalized Magnetic Nanoparticles.NSTI Nanotechnology Conference and Trade Show, 2006).*

* cited by examiner

*Primary Examiner* — Karen Cochrane Carlson
*Assistant Examiner* — Natalie Moss
(74) *Attorney, Agent, or Firm* — David P. Lentini

(57) ABSTRACT

Methods, systems, devices and materials for producing biofuels under nanoscale control ("nanobiofuels") are provided. In one aspect, the invention provides method for producing a biofuel, including providing a hydrocarbon producing organism; exposing the biological hydrocarbon producing organism to conditions effective to cause substantial release of the hydrocarbon from the biological hydrocarbon producing organism; and isolating at least a portion of the hydrocarbon. At least one of the actions of providing, exposing, and isolating is performed using a corresponding nanoscale control.

14 Claims, 3 Drawing Sheets

NANOBIOFUEL PRODUCTION USING NANOSCALE CONTROL METHODS AND MATERIALS

1 CROSS-REFERENCE TO RELATED APPLICATIONS

This application claims priority under 35 U.S.C. §119(e) to provisional U.S. Patent Application Ser. No. 61/222,100, filed 30 Jun. 2009, the entire disclosure of which is incorporated herein by reference in its entirety and for all purposes.

2 BACKGROUND OF THE INVENTION

2.1 Field of the Invention

The present invention provides systems, materials and methods for producing "biofuels", a wide range of liquid, solid biomass, or biogas fuels that are in some way derived from a carbon source that can be rapidly replenished, (including, for example hydrocarbons derived from or produced by biological organisms), referred to herein as "biofuels" and "nanobiofuels" using nanoscale control methods, nanotechnological materials and principles. The present invention relates to the areas of biofuels, biophysics, nanotechnology, chemistry, and molecular biology.

2.2 The Related Art

On 20 Apr. 2010, British Petroleum's ("BP's") Deepwater Horizon off-shore oil drilling platform, located in the Gulf of Mexico about 41 miles off the Louisiana coast, exploded, burned, and sank, killing 11 and injuring 17 of the platform's approximately 130-person crew. The undersea wellhead began emitting an uncontrolled submerged plume of oil that has now become the largest environmental disaster in history, surpassing the infamous Exxon Valdez tanker spill of 1989. Official U.S. Coast Guard estimates indicate that oil is gushing in to the Gulf of Mexico at a rate of about 35,000-60,000 barrels ("bbls") each day; some estimates by environmental scientists place the rate as much as ten-fold higher. As of the present time, attempts to bring the oil plume under control have only been partly successful.

Although much remains to be learned about the details of the Deepwater Horizon disaster, including allegations of mismanagement by BP and lax oversight by the U.S. Government's Mineral Management Service, it is widely accepted that the design and location of the platform is indicative of the growing difficulties in finding and tapping new sources to satisfy the world's growing demands for increasingly scarce fossil fuels. Fossil fuels are hydrocarbons, primarily coal, petroleum (including liquid petroleum or natural gas), or other hydrocarbon-containing natural resources that are formed from the fossilized remains of dead plants and animals that are exposed often over hundreds of millions of years to heat and pressure in the Earth's crust. Oil production peaked in the 1970s, but the demand for oil has only increased in both the industrialized and developing worlds. Even the major petroleum companies have admitted that the days of easy strikes have ended. William J. Cummings, an Exxon-Mobile spokesman, commented in 2005 that "[a]ll the easy oil and gas in the world has pretty much been found. Now comes the harder work in finding and producing oil from more challenging environments and work areas." Lord Ron Oxburgh, a former chairman of Shell Oil, concurred in 2008: "It is pretty clear that there is not much chance of finding any significant quantity of new cheap oil. Any new or unconventional oil is going to be expensive." Thus, the stage has been set for Deepwater Horizon and the other rigs like it, rigs that require cutting-edge technology to obtain fossil fuels from some of the world's harshest and most remote environments.

The difficulties in finding new oil reserves mentioned above have led many petroleum industry observers to believe that the world has entered, or will soon enter, the era of "peak oil": The period during which oil production will reach its zenith and then continually dwindle. The concept of peak oil is based on the work of geologist M. King Hubbert, who developed predictive models of domestic U.S. oil production that accurately predicted its peak in the period between 1965 and 1970. Hubbert's ideas, now called "Hubbert peak theory" have been successfully applied to prediction of peak oil production in other regions, countries, fields, and even wells. Current global predictions of peak oil suggest that the maximum of production will occur some time between about 2015 and about 2020. (Some observers estimate that we have already entered the peak oil period.) After that, oil will become increasingly scarce regardless of how hard mankind searches for it. Critics of peak oil theory point to the use of new technologies to extract oil and other fossil fuels from harder-to-reach sources driven by economic incentives; but such oil would certainly be more expensive than oil from current (conventional) sources, and there is no guarantee that decreasing oil production can be alleviated by a faith in economic incentives and technology.

The effects of the current demand for riskier methods of obtaining oil and other fossil fuels, regardless of whether we have entered or will soon enter the era of peak oil, can already be felt by the current catastrophe in the Gulf of Mexico. But the economic, social, and even individual pain will only grow as the economies of the world adjust to ever scarcer oil supplies. Predictions of the severity of the effects of increasing oil scarcity run from large bouts of inflation to the collapse of industrial civilization. As countries vie for dwindling fossil fuel reserves, the risk of conflict will also grow.

Moreover, as the Exxon Valdez disaster illustrates, merely transporting the billions of barrels of oil produced each day carries risks. Tankers and port facilities have been sources of environmental damage from oil spills due to mishandling and collisions. Worse, much of the world's oil shipping passes through several geographical choke points, such as the Straits of Hormuz and Malacca, both of which are considered vulnerable to terrorist attacks and interdiction by rouge states. The Gulf of Oman, located just outside the Strait of Hormuz, has become infamous for pirate activities. The U.S. alone has spent billions in defense appropriations to maintain a high level of security in these waters.

But U.S. defense spending extends well beyond protecting the sea lanes. The U.S. and other countries have made vast commitments in money, equipment, and personnel to protect the oil producing countries such as the Arabian Peninsula. Modern large-scale industrial development and global modernization rely heavily upon fossil fuels. The growing dependence on depleting fossil fuels, such as gasoline derived from oil, is the causes of major regional and global conflicts and growing environmental concerns. There is a tremendous threat to global security not only due to competition over dwindling fossil fuel reserves, but also due to impact of burning fossil fuels on climate change and the carbon footprint on our environment.

The burning of fossil fuels by humans is the largest source of emissions of carbon dioxide, which is one of the greenhouse gases that contributes to global warming, causing the average surface temperature of the Earth to rise in response. Greenhouse gas emissions from burning fossil fuels are posing a great threat to our global and environmental security and if unchecked could eventually endanger life on this planet.

One way to delay the arrival, and offset the effects, of the decline in oil production, and the resulting threats to our security and our environment, is to encourage conservation. Allowing market forces to act as a brake on consumption, increasing mileage efficiency standards for cars, and encouraging the development of vehicles powered by other energy sources, such as electricity using nuclear power, all can ameliorate the pain expected from the loss of relatively cheap petroleum. But such efforts will not remove completely the need for oil, which will still be a vital source of lubricants, and carbon feedstocks for fertilizers, plastics, and all sorts of important chemicals such as pharmaceuticals.

Thus the world requires truly new sources of "renewable fuels" that can be rapidly replenished. We focus this invention on renewable biofuels which comprise a wide range of liquid, solid biomass, or biogas fuels that are in some way derived from a carbon source that can be rapidly replenished, (including for example hydrocarbons derived from or produced by biological organisms), referred to herein as "biofuels" and as "nanobiofuels" when using nanoscale control methods, nanotechnological materials and principles. A myriad of technologies to produce hydrocarbons that do not require fossil fuels from geological sources have been proposed and are in different stages of development. Among these nascent technologies are new methods for producing "biofuels", i.e., a wide range of liquid, solid biomass, or biogas fuels that are in some way derived from a carbon source that can be rapidly replenished, (including for example hydrocarbons derived from or produced by biological organisms), referred to herein as biofuels and as nanobiofuels when using nanoscale control methods, nanotechnological materials and principles. Biofuels include hydrocarbons that are made through or derived somehow from biological processes, especially by organisms, instead of through longer timescale geological processes. Many organisms naturally produce hydrocarbons in the form of oils that can be harvested by collecting their secretions or using cellular disruption. Two particular examples of such organisms are certain algae and termophilic microbes.

Efforts at algaculture, the farming of algae using the techniques of aquaculture, have produced a variety of biofuels (i.e., fuels derived in some way from a carbon source that can be rapidly replenished, (including for example hydrocarbons derived from or produced by biological organisms or from biomass), including vegetable oil, biodiesel, bioethanol, biogasoline, biomethanol, biobutanol among others. Typical algaculture efforts include the use of so-called "micro-algae": unicellular algal species that live individually, in chains, or in groups. Microalgae sizes can range from a few micrometers ($\mu m$) to a few hundreds of micrometers. Microalgae lack roots, stems, and leaves; so they can be cultivated in aqueous environments. Algal species currently under development for biofuel production include: *Botryococcus braunii, Chlorella, Dunaliella tertiolecta, Gracilaria, Pleurochrysis carterae*, and *Sargassum*. In particular, recent studies suggest that algae could be raised scalably in sufficient mass to produce about 200 bbl of algal oil per hectare (ha) of land. However, inefficiencies at all stages of production severely limit achievement of this theoretical amount; current processes can only produce algal oil and its derivatives at a cost of at least $60-$100/bbl, which prevents algal biofuels from viably competing with petroleum and other fossil fuels.

Certain thermophilic microbes can also produce renewable biofuels. In particular, the thermophilic microbes Ax99-59 or JH146 have been found to have the intrinsic enzymatic machinery needed to produce hydrocarbon fuels directly from $CO_2$, such as isobutanol ($CH_3CH(CH_3)CH_2OH$), a useful hydrocarbon that can be readily processed and derivatized into a wide variety of commercially valuable fuels and chemical compounds. However the development of these organisms into a commercially viable and scalable biofuel source remains to be seen.

As we enter the second decade of the $21^{st}$ Century, America and the world face daunting challenges to meeting our growing needs for renewable fuels and sources of hydrocarbons that can be rapidly replenished. As the New York Times reported (22 Jun. 2010), Americans want new energy sources, but they don't want to see increases in gasoline prices. Thus, any new source of hydrocarbons must compete against oil and gasoline prices that are still relatively cheap, largely because they do not reflect the total costs to society in terms of security and environmental damage. The present invention meets these and other needs.

3 SUMMARY OF EMBODIMENTS OF THE INVENTION

In one embodiment, the present invention provides a method for producing a biofuel. In one embodiment, the method comprises providing a hydrocarbon producing organism; exposing the biological hydrocarbon producing organism to conditions effective to cause substantial release of the hydrocarbon from the biological hydrocarbon producing organism; and isolating at least a portion of the hydrocarbon. At least one of the actions of providing, exposing, and isolating is performed using a nanoscale control corresponding to each of the at least one actions of providing, exposing, and isolating.

In more specific embodiments, the method further includes processing the isolated hydrocarbon. More specific embodiments also include exposing the hydrocarbon to a solid phase nanoscale controlled trasnesterification medium to produce a final biofuel product. In still more specific embodiments, the final biofuel product is selected from the group consisting of biodiesel and ethanol.

Other embodiments include using a nanoscale control to provide the biological hydrocarbon producing organism. In more specific embodiments, the nanoscale control to provide the biological hydrocarbon producing organism includes selecting the biological producing organism by genetic identification using a nanoscale detection process.

In still other embodiments, the action of providing includes growing the biological hydrocarbon producing organism under conditions controlled by at least one nanotechnological material. More specific embodiments include those in which the action of exposing the biological hydrocarbon producing organism to at least one nanotechnological material. Still other more specific embodiments include those in which the action of isolating includes exposing the biological hydrocarbon producing organism to at least one nanotechnological material.

In some embodiments, the biological hydrocarbon organism is an algae; in other embodiments, the biological hydrocarbon organism is a microbe, and, more particularly, a thermophilic microbe.

In another aspect, the present invention provides a biorefinery for producing nanobiofuels. In some embodiments, the biorefinery includes a biological hydrocarbon producing organism incubator; a waste collector in fluid communication with the biological hydrocarbon producing organism incubator; a bioreaction chamber in fluid communication with the biological hydrocarbon producing organism incubator; and a purification chamber in fluid communication with the bioreaction chamber. At least one of the incubator, bioreaction chamber, and purification chamber is under nanoscale control or includes at least one nanotechnological material.

Some alternative embodiments of the biorefinery further include a second bioreaction chamber. Still others further include a membrane separating the bioreaction chamber from the second bioreaction chamber. Yet other embodiments further include a refining chamber. And still other embodiments further include a membrane separating the refining chamber from the bioreaction chamber.

4 BRIEF DESCRIPTION OF THE DRAWINGS

Exemplary embodiments of the present invention are described herein with reference to the following drawings, in which.

5 DETAILED DESCRIPTION OF SOME EMBODIMENTS OF THE INVENTION

5.1 Overview

Figure 1:
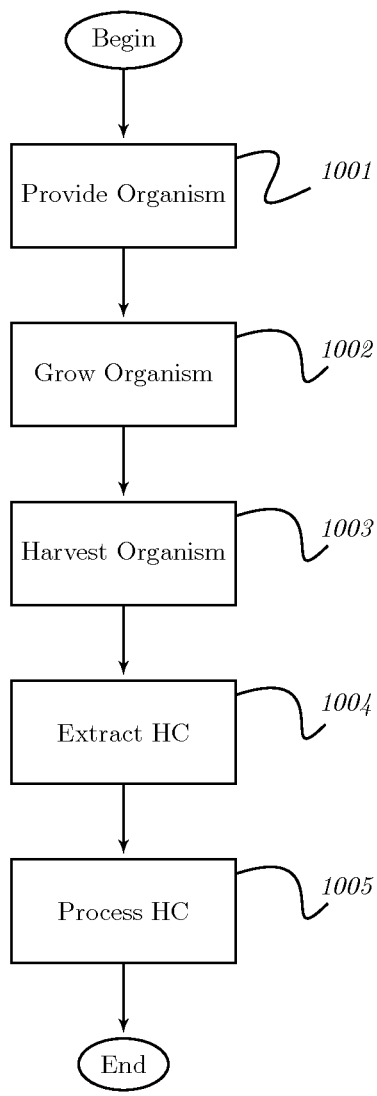
FIG. 1 is a flowchart illustrating a method for obtaining hydrocarbons from algae in accordance with one embodiment of the invention.

The present invention provides the novel insight that nanoscale control and nanotechnological methods and materials and methods (i.e., methods based on the application of nanotechnological materials and insights of material interactions at the nanoscale) provide unique advantages over traditional methods of producing biofuels. As used herein, "nanoscale" or "nanotechnological" refers to technologies or methods that are based on the ability to probe, measure, manipulate, produce, or control systems at a scale at or below about 100 nanometer (nm). "Precision Control" as used herein refers to the ability to control systems at a scale at or below about 100 nm. As those having ordinary skill in the art will understand, interactions at nanoscale or nanotechnological distances can be markedly different from the interactions at scales greater than 100 nm. In terms of controlling processes, such as processes for producing biofuels from organisms, chemical or biochemical reactions, the ability to produce and precision control such processes at the nanoscale can bestow several unanticipated benefits and advantages than have heretofore been possible by traditional "macroscale processes" such as bulk production processes or macroscopic control and manipulation methods. Examples of such conventional macroscale processes include but are not limited to controlling pH of a solution by adding acids or bases in bulk to a mixture, filtering organisms in bulk using membrane filters. By relying on thermodynamic and bulk (macroscopic) physical principles, macroscale processes are based on large statistical averages of entire populations of chemical or biochemical species; such averages are often too coarse to enable careful precision control and optimization of the process. Thus, current methods for producing biofuels are macroscopic bulky methods and consume large amounts of energy, produce large amounts of waste product for every unit of desired product, and rely chiefly upon diffusion and Brownian motion to facilitate the largely random interactions among all of the agents, ingredients, or species present in the mixture.

In sharp contrast, the processes, methods, materials, and devices provided by the present invention utilize nanoscale or nanotechnological controls to produce a finer level of precision control over biofuel production processes. Without wishing to bound to any particular theory of action, such finer control or precision control or nanoscale control and detection capabilities enables much greater precision in measurements of key control parameters as well as much greater precision and accuracy in fine-tuning these control parameters. These nanoscale methods enable a much greater sensitivity to chemical and organismal identity and outputs when processes can be controlled and influenced at nanotechnological distances, as will be described in greater detail herein below. In particular, the processes of the invention provide greater precision control, nanoscale control, and accuracy with respect to the organisms used in the production of biofuels and enable the tuning of the system to drive the selected production of a desired metabolite over unwanted products. Thus, this invention discloses nanoscale methods to genetically and metabolically fine tune organisms and downstream production processes to maximize the production of desired products and hence increase the yield of biofuel production.

In conjunction with the greater degree of precision, specificity, accuracy and, ultimately, control of the various steps of the production process (either individually, wholly, or in some combination of each step and sub-process thereof), the present invention further includes the use of mathematical modeling in conjunction with the nanoscale methods and materials and processes described herein to obtain further improvements in biofuel production efficiency. As will be apparent to those having ordinary skill in the art upon reading the description of the present invention herein, the use of mathematical modeling, e.g., using network and systems theory, based on the capacity of nanotechnological processes to measure conditions and deliver reagents with greater precision and accuracy than available using the sorts of macroscopic controls traditionally available, will provide even greater process optimization than expected using conventional techniques. More particularly, the methods and materials provided by the present invention can reduce the cost of biofuel from algae from a current rate of about $60/bbl to less than about $10/bbl, more particularly less than about $6/bbl, and still more particularly less than about $1/bbl.

5.2 Definitions

As used herein, the term "hydrocarbon" refers to any chemical compound containing hydrogen and carbon that has utility as a biofuel or a precursor to a biofuel and that can be produced by, or derived from, a naturally occurring or genetically modified organism. The term "hydrocarbon" as used herein includes both straight-chain and branched and cyclic molecules, aliphatic and aromatic molecules (and combinations thereof), and further extends beyond compounds composed exclusively of hydrogen and carbon (e.g., methane, ethane, and propane) to include substitutions such as, but not limited to, hydroxy (OH), thio (SH), halogen (F, Cl, Br, I), carboxy (COOH), and carbonyl (=O).

As used herein, the term "biofuel" refers generally to any of a wide range of liquid, solid biomass, or biogas fuels that are in some way derived from a carbon source that can be rapidly replenished, (including for example hydrocarbons derived from or produced by biological organisms), referred to herein as "biofuels" and "nanobiofuels" when using nanoscale control methods, nanotechnological materials and principles.

As used herein, an "organism" is any contiguous life form or system, living or dead, especially one that at some point was capable of growth and reproduction. In particular, "organism" as used herein includes, but is not limited to, bacteria, macro-algae, and micro-algae, animal, plant, fungus, or other micro-organism.

5.3 Processes for Making Biofuels Under Nanoscale Control

5.3.1 From Algae and Microalgae

In a first aspect, shown at 1000 in FIG. 1, the present invention provides methods and materials for making biofuels under nanoscale control using algae. At 1001, algae suitable for making a biofuel are provided. In more specific embodiments, the algae are micro-algae. In still more specific embodiments, the micro-algae are selected from the group consisting of: *Botryococcus braunii, Chlorella, Dunaliella tertiolecta, Gracilaria, Pleurochrysis carterae*, and *Sargassum*. In still more specific embodiments, the micro-algae are *Botryococcus braunii* or *Chlorella*. Any of the foregoing algae and micro-algae can be in a natural (i.e., wild-type) genetic state, or the algae and micro-algae can be genetically modified. The methods and materials for growing such algae and micro-algae are known to those having ordinary skill in the art, for example as described in U.S. Pat. No. 7,536,827 and in published U.S. patent applications, publication numbers: 20100112649, 20100159579, 20100159567, 20100159539, 20100154293, 20100151545, 20100139265, 20100130763, 20100124774, 20100120111, 20100120095, 20100112649, 20100105573, 20100105129, 20100099146, 20100093046, 20100081835, 20100081798, 20100081178, 20100077654, 20100068772, 20100064573, 20100050502, 20100041120, 20100035320, 20100031395, 20100028977, 20100028966, 20100021968, 20100021912, 20100009423, 20090325264, 20090325253, 20090305942, 20090305389, 20090298159, 20090294354, 20090291469, 20090288337, 20090286294, 20090269839, 20090253169, 20090246766, 20090215179, 20090215140, 20090211150, 20090209015, 20090203115, 20090203070, 20090181438, 20090181434, 20090163729, 20090158638, 20090151020, 20090148931, 20090148928, 20090137013, 20090130706, 20090119978, 20090113572, 20090084025, 20090081748, 20090077863, 20090064567, 20090056201, 20090053765, 20090047722, 20090019608, 20090011492, 20080319287, 20080311649, 20080296219, 20080289067, 20080268302, 20080233613, 20080220515, 20080220486, 20080213835, 20080188676, 20080184384, 20080176304, 20080167214, 20080160593, 20080160591, 20080155888, 20080124446, 20080118964, 20080057177, 20080052987, 20080038805, 20080009055, 20070196892, 20070118930, 20070118916, 20060218671, 20060110797, 20060075519, 20060053514, 20050260553, 20050239182, 20050214920, 20050064577, 20050048619, 20040253702, 20040197890, and 20040067569, each of which is incorporated herein by reference in its entirety and for all purposes. In other embodiments, the algae is a macroalgae, and, in more specific embodiments, the macroalgae is *Chlorophycede Cladophura*.

In some embodiments, the algae are first selected for superior production characteristics. For example, algae can be selected for superior hydrocarbon production or other favorable property, alone or in combination. In a more specific embodiment, a nanoscale detection process (for example, Gene-RADAR® from Nanobiosym Diagnostics, Inc.) is used to identify, screen, genetically engineer and select optimal organism (i.e., algae, bacterial, or other microbial) strains. In one particular embodiment, the nanoscale detection process uses one or more cell surface markers to identify the algae having desirable properties. Such cell surface markers include, but are not limited to, gene fragments, polypeptides, and antigens presented on the cell surface. In another particular embodiments, nanoscale detection process (e.g. Gene-RADAR®) are used to identify, screen, genetically engineer and select optimal genetic (i.e., DNA or RNA markers) corresponding to desirable traits that lead to the most efficient and optimum biofuel production process. The correlation of performance with the identity of the organism can be done using methods and materials known to those having ordinary skill in the art. In one specific embodiment, the GENE-RADAR® platform is used to optimize the growth conditions, lipid production, and other performance parameters of various algae and other organisms to maximize the production of biofuels therein. Still other useful methods are described in U.S. Pat. No. 7,494,791, incorporated herein in its entirety and for all purposes. Another useful device for detecting and sorting cells for use with the present invention is described in U.S. Pat. No. 7,355,696, incorporated herein by reference in its entirety and for all purposes.

In other embodiments, the above-described correlation is performed as a function of the metabolic state of algae by measuring components of the metabolome of the organism. Again, those of ordinary skill in the art will be able to use the above-described techniques to perform the necessary correlations and identification.

After the selection and provision of the microbes or organism, the organism is grown in a suitable environment. The growth and cultivation of such algae will be familiar to those having ordinary skill in the art, as illustrated by the above-listed incorporated U.S. patents and published patent applications. In one exemplary embodiment, the algae are grown in a bioreactor that is tunable and nanoengineered to provide nanoscale control over various control knobs or environmental parameters that influence or enhance the biofuel production process. In another embodiment, the organisms are grown in an integrated biorefinery. One exemplary biorefinery comprises an 8-acre pond that is divided to 4 smaller raceway-type ponds on the lateral axis. Each of the raceway ponds are about 2 acres and include a single paddlewheel to impart a gentle rotation to the water in the pond. The water depth is between about 12 inches and about 18 inches and is fed fresh water from wells that is slightly saline. A bloom of the provided algae is seeded into the raceway ponds using a trailer device that also delivers catfish fry into the pond. In some embodiments, only atmospheric $CO_2$ is provided to the algae; in other embodiments additional $CO_2$ is also provided. During warm and sunny months, the algae are harvested after between about 4 months and about 6 months.

In some embodiments, magnetic nanoparticles (or submicron particles) are used to create desirable, precision controlled agitation or mixing of the water and growth medium in place of, or in addition to, the above-mentioned paddlewheel. The configuration and operation of such magnetic nanoparticle-mediated agitation will be familiar to those having ordinary skill in the art, e.g., as described in "Magnetic Mixing Creates Quite A Stir", *ScienceDaily* (DOE/Sandia National Laboratories (2009, Oct. 29), Retrieved Jun. 25, 2010), and "Use of Magnetic Nanoparticles for Mixing in Microarrays and Microsystems", Agarwal, Sandip, Ph.D. Thesis, Department of Chemical Engineering, Rice University, published on-line 3 Jun. 2009, both of which are incorporated herein by reference in their entireties and for all purposes.

In some embodiments, at least one factor for cultivating the organism is determined or controlled using a nanotechnological process, nanoscale production process, or nanoscale material. In one embodiment, the present invention includes providing light at one or more frequencies chosen to optimize the growth and desired hydrocarbon production capacity of the provided algae (or other organism) using nanoscale materials and controls. Such lighting can be provided using methods and materials available to those having ordinary skill in the art (see. e.g., Ashby, et al., *Nanomaterials, Nanotechnologies and Design: An Introduction for Engineers and Architects* (Butterworth-Heinemann 2009), which in incorporated herein by reference in its entirety and for all purposes). Other suitable exemplary nanoscale materials and methods for providing light at a desired wavelength are described in U.S. Pat. Nos. 7,235,792; 6,726,992; 7,737,632; 7,741,145; 7,728,504; 7,731,389; and 7,641,815, each of which is incorporated herein in its entirety and for all purposes. In addition, light filters using nanoscale materials can be used to provide suitable light for optimized growth; such materials are familiar to those having ordinary skill in the art as illustrated by, e.g., U.S. Pat. Nos. 7,450,306 and 7,276,685, each of which is incorporated herein in its entirety and for all purposes. In more specific embodiments, the light source is computer-controlled, and, in more particular embodiments, the light source is controlled to provide a pulsating light signal. In still more particular embodiments, the light source is a split-wavelength light source. Yet more specific embodiments include a computerized, pulsating, split-wavelength light source. Those having ordinary skill in the art can provide such light sources, e.g, as described in Gordon, J. W., and Polle, J. E. W. "Ultrahigh Bioproductivity from Algae", *Appl. Microbiol. Biotechnol.* 76:969-975 (2007), which in incorporated herein by reference in it entirety and for all purposes.

In other embodiments in which at least one factor for cultivating the algae (or other organism) is determined or controlled using a nanotechnological process or material, the factor is a chemical factor; in more specific embodiments, the chemical factor is monitored to optimize the growth and hydrocarbon production capacity of the provided algae (or other organism) using nanoscale materials and controls to develop mathematical models to control the introduction and maintenance of various nutrients and other growth inputs. In more specific embodiments, at least one nanoscale detection process, nanoscale membrane or nanoscale particle or other suitable nanoscale material is used to monitor the concentration of at least one chemical in the growth environment. Such membrane, particles, and materials are known to those having ordinary skill in the art, such as, by way of non-limiting examples, those described in U.S. Pat. Nos. 7,118,881; 7,163,659; 7,238,594; 7,336,859; 7,336,861; 7,387,877; 7,410,904; 7,425,749; 7,470,544; 7,655,269; 7,705,280; 7,733,479; and U.S. patent application Publication Nos. 20020192653, 20030207271, 20030215865, 20040106203, 20040182719, 20040214447, 20050070802, 20050124020, 20050161749, 20050176228, 20050221366, 20050279987, 20060004273, 20060068412, 20060169585, 20060180480, 20060183165, 20060207878, 20060270057, 20070012094, 20070025661, 20070116628, 20070145356, 20070147732, 20070231796, 20080024118, 20080054382, 20080094051, 20080095663, 20080129980, 20080135826, 20080204048, 20080212102, 20080280776, 20090010808, 20090014757, 20090147254, 20090215156, 20090220384, 20090278556, 20100020311, 20100021993, 20100060465, 20100129261, and 20100134286, each of which is incorporated herein in its entirety and for all purposes. In still other embodiments, such sensing is combined with trascriptomic or metabolomic information as described above to determine optimal growth conditions and monitor the progress of metabolic production of desired hydrocarbons. In more specific embodiments, the sensing just described determines the presence and optionally the amount of nutrients, salts, metabolites, and hydrocarbon products, and the pH and dissolved gas concentrations of the growth environment, or any subcombination thereof. In still more specific embodiments, the concentrations of one or more of these factors is used to develop mathematical models to optimize ambient reagent and biochemical concentrations and $CO_2$ dosing.

Returning to FIG. 1, when the algae (or other organism) have reach a sufficient stage of growth it is harvested and dried (1003). The harvesting and drying of algal crops (for example) is well known to those having ordinary skill in the art. In some embodiments, the harvesting and drying is performed using nanoscale materials, filters or nanoscale control processes that provide precision control over the harvesting and drying process, enabling thereby more efficiency of this particular step as compared to traditional macroscopic processes. For example, harvesting can be accomplished using sub-micron particles, sub-micron particles or nanoscale beads, or nanoscale particles having surfaces configured to reversibly attach to one or more surface determinants on the algae (or other organism). The nature and provision of such determinates are described above, and include without limitation, antigenic determinates, cell surface peptides, cell surface proteins, and cell surface oligonucleotides. Each of these can be matched to an antibody, ligand, or complimentary oligonucleotide sequence as will be understood by those having ordinary skill in the art. In more specific embodiments, the nanoscale beads or particles are magnetic, thereby enabling relatively direct removal of the algae (or other organism)-bound particles from the growth medium using a magnetic field. The provision of such magnetic nanoscale beads or particles is known in the art, e.g., as described in U.S. Patent Publication Nos. 20060286379, 20090148863, 20080206146, 20060233712, 20100051510, and 20090087381, each of which is incorporated herein by reference in its entirety and for all purposes. In addition, suitably derivatized magnetic nanoparticle precursors are commercially available, e.g., from Ocean NanoTech (Springdale, Ak.).

Following harvest, the hydrocarbons ("HC") are produced by, extracted, or otherwise derived from the algae (or other organism) (1004). The processes for extracting and isolating hydrocarbons, usually in the form of oils, from algae (or other organism) are known to those having ordinary skill in the art. In some embodiments, the above-described functionalized nanoparticles and magnetic nanoparticles are used in conjunction to lyse the algae (or other organism) cells and release the desired hydrocarbons. For example, functionalized nanoparticles, either in solution or as part of a solid substrate, are bound to cell surface features (described above) of the algae (or other organism). Magnetic nanoparticles are used to create agitation sufficient to induce lysis of the algae (or other organism) cell walls, thereby causing release of the hydrocarbons. In some more specific embodiments, ultrasound energy is applied in conjunction with the magnetic nanoparticle agitation to facilitate cell lysis. The application of such ultrasound energy to facilitate cell lysis will be understood by those having ordinary skill in the art.

In some embodiments, nanoparticles or nanofilters (or both) are used to facilitate extraction of the hydrocarbons. As noted above, the nanoparticles and nanofilters can be provided freely in solution or immobilized on a substrate, or in some combination thereof. Such materials and their use will be known by those having ordinary skill in the art. Examples of suitable nanofilters and their use can be found in U.S. Pat. No. 7,145,031, and in U.S. patent application Publication Nos.: 20090218285, 20030116510, 20090270609, and 20050084544; additional teachings are presented in Park, Eugene and Barnett, S. M. "Oil/Water Separation Using Nanofiltration Membrane Technology", *Separation Science and Technology* 36(7):1527-1542 (2001); each of the foregoing patents and published patent applications is incorporated herein in its entirety and for all purposes.

Once the lysis and collection of the released hydrocarbon is complete, the bound cellular debris and other biomass can be removed. Alternatively, the cellular debris and biomass can be removed prior to the extraction. Such operations will be familiar to those having ordinary skill in the art.

The isolated hydrocarbon is then subjected to processing (1004) to make a desired biofuel or precursor thereof. Such processing will be familiar to those having ordinary skill in the art. In some embodiments, the present invention uses derivatized sub-micron beads, nanoparticles, or nanomembranes (or a combination thereof) to facilitate the conversion process. Examples of such nanoparticles include ZnO nanoparticles as described in Yan, S., et al., "Long Term Activity of Modified ZnO Nanoparticles for Transesterification", *Fuel*, (In Press, Corrected Proof, Available online 1 Jun. 2010); and U.S. patent application Publication Numbers 20080155888, 20090005582, and 20090155864; each of the foregoing being incorporated herein by reference in its entirety and for all purposes.

5.3.2 From Microbes

A wide variety of bacteria and other microbes are known to have utility in producing biofuels (see, e.g., "Bacteria converted into 'mini-factories' for biofuels and vaccines", *ScienceDaily* (Retrieved Jun. 25, 2010, from http://www.sciencedaily.com/releases/2010/06/100608211606.htm) and Antoni, D., et al., "Biofuels from Microbes", *Applied Microbiology and Biotechnology*, 77(1):23-35 (November, 2007) (available online from SpringerLink Saturday, Sep. 22, 2007), each incorporated herein by reference in its entirety and for all purposes. Using the methods and materials discussed herein, biofuels from such bacteria can be made with the same advantages as discussed above for algae (or other organism)-produced biofuels. In some embodiments, thermophilic microbes, such as Ax99-59 or JH146, are used to produce biofuels. These microbes have been shown to produce 2-oxoisovalerate, a metabolic precursor to the useful hydrocarbon isobutanol, directly from $CO_2$, and thus are attractive sources of biofuel in view of their direct conversion of $CO_2$ and lack of need for feedstocks.

Figure 2:
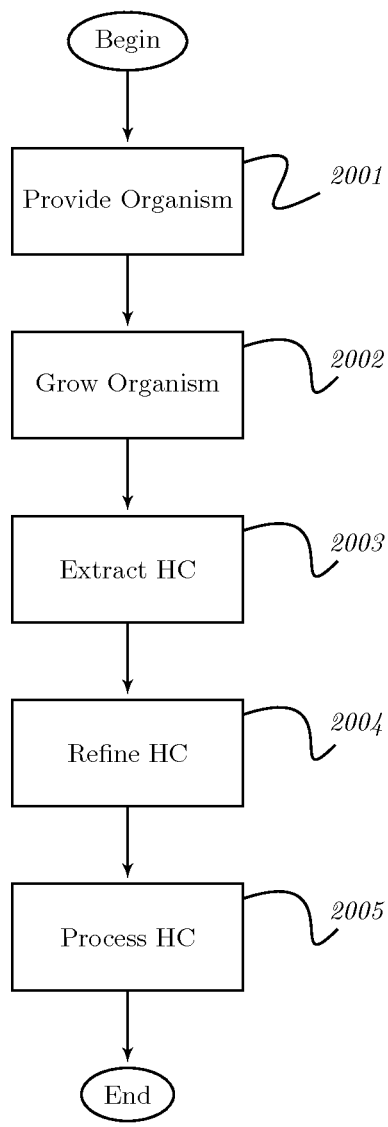
FIG. 2 is a flowchart illustrating a method for obtaining hydrocarbons from thermophilic bacteria in accordance with one embodiment of the invention.

A exemplary method for generating biofuel from microbes (e.g., Ax99-59 or JH146) is illustrated in FIG. 2. As described above, a biofuel-producing organism (e.g, a microbe) is provided (2001). In some embodiments, the wild-type forms of these two microbes are used. In other embodiments the microbes are modified using nanotechnological materials and methods. Among the latter embodiments, the techniques and methods described above for biofuel production from algae (or other organism) are used to improve or enhance the biofuel production capacity or efficiency of the organism. For example in some embodiments, nanoscale detection processes or nanoscale techniques, such as using the above-mentioned GENE-RADAR® technology, are used to identify strains and mutants having superior traits and qualities for biofuel production.

In more particular embodiments, the Ax99-59 or JH146 microbe (or both) is genetically or metabolically engineered to enhance, and in some embodiments selectively drive, productive capacity. In one embodiment, the enhancement includes providing one or more enzymes useful to enhance production of isobutanol from $CO_2$, and more particular, from $CO_2$ using a non-photosynthetic autotrophic pathway. Such methods and materials will be familiar to those having ordinary skill in the art. In other embodiments, the metabolic networks of the microbes are mapped using the methods and materials described above for monitoring metabolism and gene expression, and the metabolic pathways are then influenced or modified to enhance isobutanol production. Such techniques are familiar to those having ordinary skill in the art. In still other embodiments, electromagnetic and mechanical stresses are applied to the organisms to enhance isobutanol production.

In other embodiments, the Ax-99-59 and JH146 microbes are engineered genetically to follow autotrophic metabolic pathways for the autotrophic conversion of 2-oxoisovalerate to isobutanol. In a more specific embodiment, the genetic engineering includes providing for the expression of the heterologous enzymes Fd oxidoreductase and alcohol dehydrogenase. Such engineering can be achieved using methods and materials known to those having ordinary skill in the art. In still more specific embodiments, the above-described methods for metabolic tuning are applied to the engineered microbes to enhance the efficiency of conversion.

In another exemplary embodiment, a different set of genetic modifications are applied to the microbial genomes to enable non-photosynthetic autotrophic conversion $CO_2$ to, first, isobutyraldehyde ($CH_3CH(CH_3)CHO$), and second, to isobutanol by cloning genes for the necessary reduction of the aldehyde to the alcohol. In one embodiment, this is accomplished by engineering the bacteria to produce isovalerate decarboxylase and alcohol dehydrogenase. Such engineering can be achieved using methods and materials known to those having ordinary skill in the art. In still more specific embodiments, the above-described methods for metabolic tuning are applied to the engineered microbes to enhance the efficiency of biofuel production. In still more specific embodiments, the above-described methods for metabolic tuning and optimizing biofuel production are achieved by using tunable "nanoengineered" bioreactors that enable precision control or nanoscale control over various environmental parameters or "control knobs".

After selection, the microbes are grown under conditions effective to enable hydrocarbon production (FIG. 2 at 2002). In more specific embodiments, the microbes are Ax99-59 or JH146 (or both) and the hydrocarbon is isobutanol. Such techniques are familiar to those having ordinary skill in the art. In some embodiments, the microbes are grown using high-density cell packing by immobilizing the microbes on derivatized magnetic nanoparticles or beads as described above, or on sub-micron beads as will be familiar to those having ordinary skill in the art, in a three-dimensional ("3-D") matrix. In still other embodiments, turbulent flows in the cell growth medium are created using magnetic nanoparticles or sub-micron beads as described above. Such matrices can be made by those having ordinary skill in art in conjunction with the teachings herein.

In some embodiments, the genetic and metabolic performance of the microbes is monitored and controlled as described above; and the resulting information is used to create mathematical models that allow optimization of growth conditions and the production of the hydrocarbon (isobutanol in the case of the Ax99-59 or JH146 microbes), using methods and materials available to those having ordinary skill in the art. In one embodiment, Ax99-59 or JH146 microbes are tuned metabolically to enhance the efficiency of $CO_2$ fixation and the expression of enzymes effective to convert acetyl-CoA to 2-oxoisovalerate.

In some embodiments, the growth medium is monitored and controlled as described above to enhance the efficiency of isobutanol production.

Following growth of the microbes, the hydrocarbon product (e.g., isobutanol in those embodiments in which the microbes is Ax99-59 or JH146) is extracted (2003), refined (2004), and processed (2005) as substantially as described above and apparent to those having ordinary skill in the art.

5.4 Devices for Making Biofuels Under Nanoscale Control

In a second aspect, the present invention provides a tunable bioreactor configured to produce biofuels under nanoscale control also referred to herein as a "biorefinery".

Figure 3:
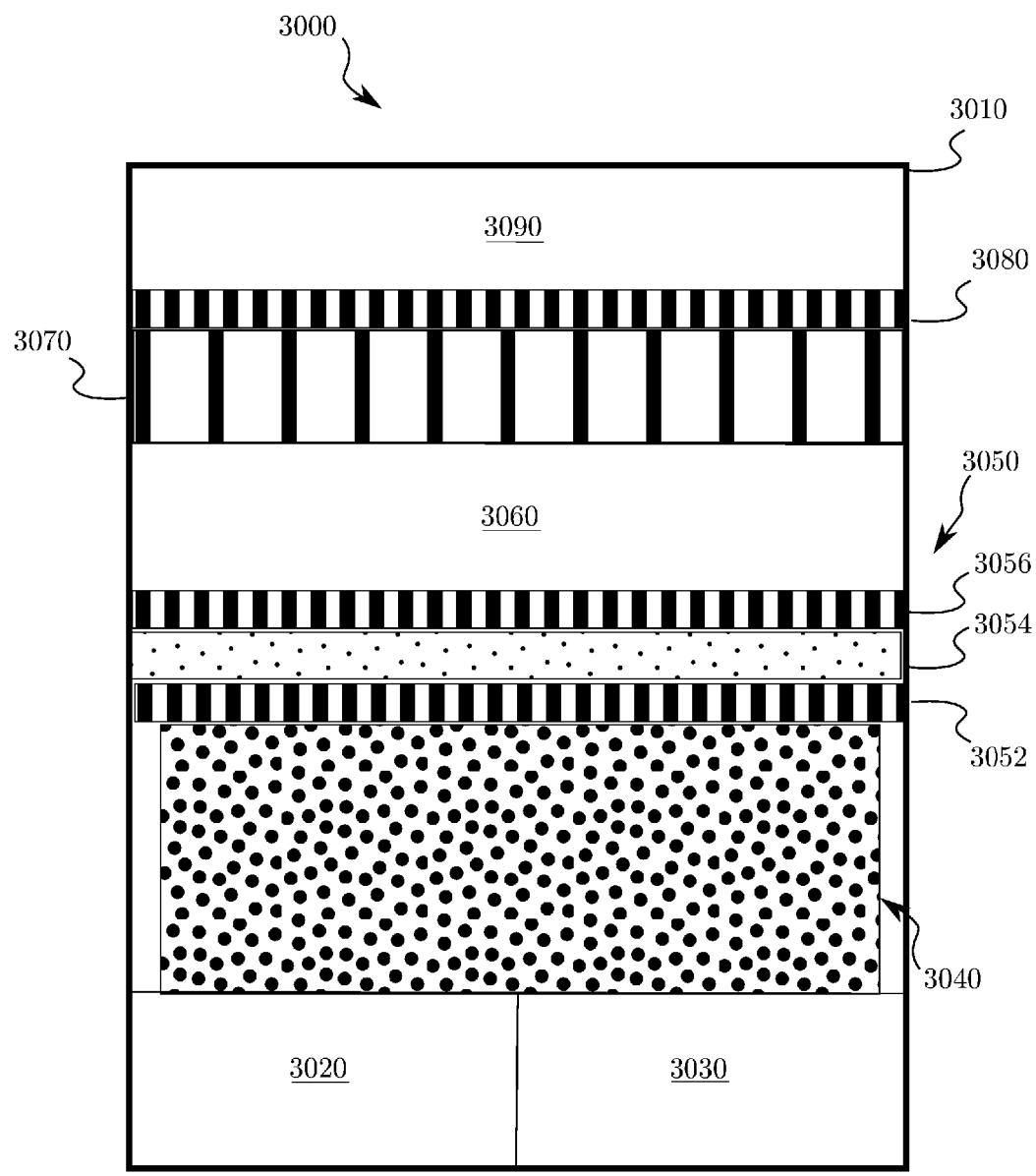
FIG. 3 is an illustration of a point-of-use "bioreactor" in accordance with one embodiment of the present invention.

One embodiment of such a bioreactor is shown at 3000 in FIG. 3. There, a housing 3010 constructed to enclose the bioreactor components described below using materials and methods familiar to those having ordinary skill in the art encases a chemical input storage tank 3020, which is dimensioned and constructed of materials configured to contain and provide the chemical inputs necessary to run the bioreactor as described further below. A waste chamber 3030 is dimensioned and configured to contain waste products from the bioreactor's operation as described further below. Chemical input storage tank 3020 and waster chamber 3030 also include various pumps, sensors, controls, and conduits that are not shown; but the inclusion, configuration, and operation of which will be apparent to those having ordinary skill in the art.

Bioreaction chamber 3040 contains the organisms and materials necessary to produce the biofuel as described above. In addition, various nanoscale solid supports and magnetic nanoparticles as described above are provided as described above to enable the necessary mixing and lysing of the microbes to release hydrocarbon into the reaction mixture as described above. Chamber 3040 also includes various sensors, controls, pumps and filters that are not shown, but which will be understood by those having ordinary skill in the art.

In one embodiment, the organisms are Ax99-59 or JH146 microbes (or both), either wild-type or genetically modified as described above. In a more specific embodiment, the organisms are Ax99-59 or JH146 microbes modified as described herein to produce isobutanol as described above. In such embodiments, chemical input storage tank provide all necessary nutrients as well as $CO_2$ and $H_2$ to enable the microbes to produce isobutanol. In a more particular embodiment, the microbes are bound to micron-sized particles or nanobeads arranged in a 2-D or 3-D matrix; more specifically, the matrix provides a relatively high packing density. In still more specific embodiments, microfluidic or nanofluidic channels are provided in the matrix to enable the motion of small molecules and dissolved gasses through the matrix to either the waste chamber or the supplemental or purification chambers described below. In some embodiments, magnetic nanoparticles are also provided, and chamber 3040 is configured to produce a magnetic field sufficient to induce the magnetic nanoparticles to create turbulence in the reaction medium sufficient to both mix the reactants and products in the chamber and cause separation of the isobutanol product from the waste products. (The process of mixing and separation using nanoscale methods or precision control processes is referred to herein as "nanoscale mixing" and "nanoscale separation", respectively.) More specifically, the turbulence will cause at least a substantial fraction of the isobutanol to move into additional reaction and purification chambers (described below) while the cellular debris and other waste materials moves into waste chamber 3030, e.g., by moving the matrix into the waste chamber using a nanofilter or nanomembrane. Those having ordinary skill in the art will understand how to configure and provision the bioreaction chamber.

In another embodiment, the Ax99-59 or JH146 are wild-type, and the intermediate 2-oxoisovalerate produced by the microbes passes through a supplemental reaction zone 3050. The supplemental reaction zone 3050 includes a supplemental reaction chamber 3054 containing additional enzymes (described above) that enable production of isobutanol from 2-oxoisovalerate as described above. The supplemental reaction chamber includes the additional enzymes described above mounted on particles or nanobeads, and is separated from the reaction chamber 3040 by a nanoscale separation process 3052 such that 2-oxoisovalerate rising from the reaction chamber 3040 enters the supplemental reaction chamber 3054 and is converted to isobutanol by the bound enzymes. The supplemental reaction chamber also includes nanoscale mixing processes, such as magnetic nanoparticles, and is configured to provide a magnetic field to induce turbulence and mixing. Provision of these elements can be accomplished using methods and materials known to those having ordinary skill in the art.

The isobutanol product, whether produced directly in reaction chamber 3040 or in supplemental reaction chamber 3054, passes through a nanoscale separation process, such as nanofilter 3056, and into a purification chamber 3060, which includes filters and other materials sufficient to provide substantially pure isobutanol. Provision of these elements can be accomplished using methods and materials known to those having ordinary skill in the art.

Some embodiments include an additional reaction zone 3070, separated from the purification chamber by a nanoscale separation process, such as a nanofilter (not shown), where additional bead-bound enzymes transform isobutanol into higher-order hydrocarbons, such as octanes and aromatic hydrocarbons. More specifically, bound enzymes convert isobutanol into isobutylene, which can be transformed by additional enzymes and reagents into a wide variety of products. For example, conversion of isobutylene into isooctene allows production of "bio-gasoline", "bio jet fuel", "biodiesel", and similar products. Alternatively, the isooctene can be converted into aromatic compounds, including xylene, which can be further converted into terephthalic acid and various polymers. Alternatively, the isobutylene can be converted into methyl methacrylate ("MMA"), butyl rubber, and other compounds. The desired product pass through a nanoscale separation process, such as nanofilter 3080, and into a storage chamber 3090 from which the product can be retrieved (e.g., by pumping). Provision of these elements can be accomplished using methods and materials known to those having ordinary skill in the art.

As noted above, the various reaction and storage chambers will include sensors and devices necessary to enable the mixing and collecting of materials and removal of debris. In some embodiments, most, if not all, of these operations are controlled by computers that collect and operate on data provided by the sensors. Thus, in some embodiments, the bioreactor provided by the invention is substantially automated. Provision of these elements can be accomplished using methods and materials known to those having ordinary skill in the art.

6 CONCLUSION

Thus the advantages of the present invention will be apparent. Using the materials, methods, and devices described herein, important biofuels can be produced with high yield and low cost, and without the expense and risk inherent in obtaining the same hydrocarbons from geological petroleum sources. Importantly, the processes described herein for producing the biofuels consume $CO_2$, a significant greenhouse gas. Thus, the present invention provides an important advance in so-called "carbon-neutral" energy sources and reducing an important greenhouse gas by creating hydrocarbon fuels from $CO_2$, a principle greenhouse gas produced by combustion.

The above description of the embodiments, alternative embodiments, and specific examples, are given by way of illustration and should not be viewed as limiting. Further, many changes and modifications within the scope of the present embodiments may be made without departing from the spirit thereof, and the present invention such changes and modifications.

What is claimed is:

1. A method for producing a biofuel, comprising:
providing a biological hydrocarbon producing organism, said providing including selecting said biological hydrocarbon producing organism using a nanoscale detection process, said providing further including growing said biological hydrocarbon producing organism under conditions controlled by at least one nanotechnological material or process;
exposing said biological hydrocarbon producing organism to conditions effective to cause substantial release of a hydrocarbon from said biological hydrocarbon producing organism;
isolating at least a portion of said hydrocarbon; and
processing said isolated hydrocarbon to produce said biofuel.

2. The method of claim 1, wherein said exposing includes exposing said biological hydrocarbon producing organism to at least one nanotechnological material.

3. The method of claim 1, wherein said isolating includes exposing said biological hydrocarbon producing organism to at least one nanotechnological material.

4. The method of claim 1, further including growing algae under conditions controlled by at least one nanotechnological material.

5. The method of claim 4, further including harvesting and drying said algae using at least one nanotechnological material.

6. The method of claim 1, further including growing bacteria under conditions controlled by at least one nanotechnological material.

7. The method of claim 6, further including extracting said hydrocarbon using at least one nanotechnological material.

8. The method of claim 1, wherein said nanoscale detection process is used to identify at least one cell surface marker on said biological hydrocarbon producing organism.

9. The method of claim 8, wherein said cell surface marker is selected from the group consisting of: gene fragments, polypeptides, and antigens.

10. The method of claim 9, wherein said cell surface marker is a gene fragment.

11. The method of claim 10, wherein said nanoscale detection process includes using a non-thermally driven polymerase chain reaction method.

12. The method of claim 11, wherein said non-thermally driven polymerase chain reaction method is a controlled tension polymerase chain reaction method.

13. The method of claim 12, wherein said nanoscale detection process is performed using GeneRADAR®.

14. The method of claim 1, further including optimizing said conditions effective to cause substantial release of a hydrocarbon by detecting at least one cell surface marker on said biological hydrocarbon producing organism and correlating the release of hydrocarbon with the detection of said cell surface marker, and adjusting said conditions according to said correlating.

* * * * *